(12) United States Patent
Schwarz et al.

(10) Patent No.: US 8,097,646 B2
(45) Date of Patent: Jan. 17, 2012

(54) OPHTHALMIC PREPARATION CONTAINING MENTHYL ESTER OF INDOMETHACIN

(75) Inventors: Joseph Schwarz, Richmond Hill (CA); Michael Weisspapir, Toronto (CA)

(73) Assignee: AlphaRx, Inc., Central (HK)

( * ) Notice: Subject to any disclaimer, the term of this patent is extended or adjusted under 35 U.S.C. 154(b) by 1408 days.

(21) Appl. No.: 11/593,469

(22) Filed: Nov. 7, 2006

(65) Prior Publication Data

US 2007/0116777 A1 May 24, 2007

Related U.S. Application Data

(60) Provisional application No. 60/733,756, filed on Nov. 7, 2005.

(51) Int. Cl.
*A61K 31/40* (2006.01)
(52) U.S. Cl. ........................................ 514/420; 514/912
(58) Field of Classification Search .................. 514/420, 514/912
See application file for complete search history.

(56) References Cited

U.S. PATENT DOCUMENTS

| | | | |
|---|---|---|---|
| 4,613,505 | A | 9/1986 | Mizushima et al. |
| 5,171,566 | A | 12/1992 | Mizushima et al. |
| 5,364,632 | A | 11/1994 | Benita et al. |
| 5,496,811 | A | 3/1996 | Aviv et al. |
| 5,998,465 | A | 12/1999 | Hellberg et al. |
| 6,306,890 | B1 | 10/2001 | Kalgutkar et al. |
| 6,762,182 | B1 | 7/2004 | Kalgutkar et al. |

OTHER PUBLICATIONS

Mizushima, Y. Basic and Clinical Studies of Prodrugs of Nonsteroidal Anti-inflammatory Drugs. Pharmacology, 1982, 25 (Suppl.1) pp. 39-45.
Salva P, Costa J, Andreu D, Notivol R, Martinez M. Tolerability and Safety of 0.1% Diclofenac Plus 0.3% Tobramycin Fixed-Dose Ophthalmic Solution: A Randomized, Comparative, Controlled Study in Healthy Volunteers. Methods and Exp Clin Pharmacol. Apr. 1999;21(3):203-8.
Scuderi B, Driussi GB, Chizzolini M, Salvetat ML, Beltrame G. Effectiveness and Tolerance of Piroxicam 0.5% and Diclofenac Sodium 0.1% in Controlling Inflammation After Cataract Surgery. Eur J Ophthalmol. Jul. 2003; 13(6):536-40.
McCarey B., Napalkov J., Pippen P., Roester J. and Al Reavers T. Corneal Would Healing Strength With Topical Antiinflammatory Drugs. Cornea, 1995, 14:290-294.
Stroobants A., Fabre K. Maudgal P. Effect of Non-Steroidal Anti-Inflammatory Drugs (NSAID) on the Rabbit Corneal Epithelium Studied by Scannning Electron Microscopy Bull. Soc. Belge Ophtalmol., 276, 73-81, 2000.
Diestelhorst M, Schmidl B, Konen W, Mester U, Raj PS. Efficacy and Tolerance of Diclofenac Sodium 0.1%, Flurbiprofen 0.03% and Indomethacin 1.0% in Controlling Postoperative Inflammation. J Cataract Refract Surg. 1996; 22 Suppl 1:788-93.
Aggarwal D, Kaur IP. Improved Pharmacodynamics of Timolol Maleate From a Mucoadhesive Nidsomal Ophthalmic Drug Delivery System. Int J Pharm. Feb. 16, 2005; 290(1-2): 155-9.
Mainardes RM, Urban MC, Cinto PD, Khalil NM, Chaud MV, Evangelista RC, Gremiad MP. Colloidal Carriers for Ophthalmic Drug Delivery. Curr Drug Targets. May 2005; 6(3): 363-71.
De TR, Bergey EJ, Chung SJ, Rodman DJ, Bharali DJ, Prasad PN. Polycarboxylic Acid Nanoparticles for Ophthalmic Drug Delivery: An Ex Vivo Evaluation With Human Cornea. J Microencapsul. Dec. 2004;21(8):841-55.
Calvo P, Alonso MJ, Vila-Jato JL, Robinson JR. Improved Ocular Bioavailability of Indomethacin by Novel Ocular Drug Carriers. J Pharm Pharmacol. Nov. 1996; 48(11):1147-52.
Remington: The Science and Practice of Pharmacy, 20th edition, Lippincott, Williams and Wilkins, Philadelphia, 2000.
Mizushima Y., "Basic and Clinical Studies of Prodrugs of Nonsteroidal Anti-Inflammatory Drugs," Pharmacology, 1982, 25 (Suppl. 1):39-45.
Salva, et al., "Tolerability and Safety of 0.1% Diclofenac Plus 0.3% Tobramycin Fixed-Dose Opthalmic Solution: A Randomized, Comparative, Controlled Study in Healthy Volunteers," Methods Find Exp. Clin. Pharmacol.,1999, 21 (3):203-8.
Scuderi, et al., "Effectiveness and Tolerance of Piroxicam 0.5% and Diclofenac sodium 0.1% in controlling inflammation after cataract surgery," Eur J Opthalmol., 2003, 13(6):536-40.
McCarey, et al., "Corneal wound healing strength with topical antiinflammatory drugs," Cornea, 1995, 14(3):290-294.
Stroobants, et al., "Effect of Non-Steroidal Anti-inflammatory drugs (NSAID) on the Rabbit Corneal Epithelium studied by scanning electron microscopy," Bull. Soc. Belge Ophtalmol., 2000, 276:73-81.
Diestelhorst, et al., "Efficacy and Tolerance of Diclofenac sodium 0.1%, Flurbiprofen 0.03%, and indomethacin 1.0% in controlling postoperative inflammation," Abstract Only, J. Cataract Refract Surg., 1996, 22(Suppl. 1):788-93.
Aggarwal, et al., "Improved pharmacodynamics of timolol maleate from a mucoadhesive niosomal opthalmic drug delivery system," Int. J. Pharm. 2005, 290:155-59.
Mainardes, et al., "Colloidal Carriers for Ophthalmic Drug Delivery," Curr. Drug Targets. 2005, 6(3):363-71.
De, et al., "Polycarboxylic acid nanoparticles for ophthalmic drug delivery—an ex vivo Evaluation with Human Cornea," J Microencapsul., 2004, 21(8):841-55.
Calvo, et al., "Improved Ocular Bioavailability of Indomethacin by Novel Ocular Drug Carriers," J Pharm Pharmacol., 1996, 48(11):1147-52.
Lang, et al., "Ophthalmic Preparations," Remington: The Science and Practice of Pharmacy, Chapter 43, 20th Edition, Lippincott, Williams and Wilkins, Philadelphia, 2000, pp. 850-866.

*Primary Examiner* — Zohreh Fay
(74) *Attorney, Agent, or Firm* — Mayer Brown LLP

(57) ABSTRACT

There is provided an ophthalmic pharmaceutical preparation comprising menthyl ester of indomethacin as an active ingredient. Also provided are different possible formulations of the ophthalmic preparation, and different methods of treating ophthalmic irritation using the ophthalmic preparation.

6 Claims, 3 Drawing Sheets

Indomethacin
MW 357.8

L-Menthol
MW 156.3

Menthyl ester of Indomethacin
MW 496.05

OPHTHALMIC PREPARATION CONTAINING MENTHYL ESTER OF INDOMETHACIN

RELATED APPLICATIONS

This application claims priority from filed U.S. Provisional Patent Application Ser. No. 60/733,756, entitled, "Ophthalmic Preparation Containing Menthyl Ester of Indomethacin", filed Nov. 7, 2005.

FIELD OF THE INVENTION

This invention relates to an ophthalmic pharmaceutical preparation comprising menthyl ester of indomethacin and to the use of said preparation for the treatment of inflammation of the eye.

BACKGROUND OF THE INVENTION

Indomethacin [1-(4Chlorobenzoyl)-5-Methoxy-2-methyl-1H-indole-3-acetic acid] has superior anti-inflammatory, analgetic and antipyretic activities and is used in the form of capsules (Indocin®) for treatment of systemic inflammatory diseases (arthritis, muscle pain, tendonitis, etc.). Sodium salt of indomethacin may be injected intravenously or used for treatment of inflammatory conditions in the eye (Indocollyre®).

Indomethacin is practically insoluble in water. Solubility in water media improves with increased pH, but the produced solution of indomethacin salt is very unstable and degrades quickly, forming inactive compounds. Additionally, either indomethacin itself or sodium salt of indomethacin are highly irritating to mucous surfaces, causing stinging and burning sensations. Furthermore, extended use almost definitely produces ulceration.

In order to decrease such irritation, different derivatives of indomethacin have been explored. Multiple esters, amides, Mannich bases, and some other hydrolysable compounds were synthesized. Such modification usually leads to a decrease in ulcerogenicity and a decrease of local irritation, along with an increase in lipophilicity. In some cases, such modification has resulted in modified cyclooxygenase inhibition selectivity. For instance, indomethacin is a non-selective COX-1/COX-2 inhibitor, while many of its esters and other derivatives are described as selective COX-2 inhibitors. [U.S. Pat. No. 6,306,890 ("Esters Derived from Indolealkanols and Novel Amides Derived from Indolealkylamides that are Selective COX-2 Inhibitors") and U.S. Pat. No. 6,762,182 ("Converting COX Inhibition Compounds that are not COX-2 Selective Inhibitors to Derivatives that are COX-2 Selective"), both to Kalgutkar et al.].

Different formulations of NSAIDs are used for the treatment of ophthalmic inflammation conditions. For example, Diclofenac sodium 0.1% (Voltaren® ophthalmic, Novartis), Bromfenac 0.09% (Xibrom®, ISTA/Senju Pharmaceuticals), Flurbiprofen sodium 0.03% (Ocufen®, Allergan, Bausch & Lomb), Indomethacin sodium 0.1% (Indocin® Ophthalmic, Merck, Indocollyre®, Chauvin) and 1.0% Indomethacin sodium (Indoptol®, Merck Sharp & Dohme), and Ketorolac tromethamine 0.5% (Acular®, Allergan) for ophthalmic applications are manufactured and marketed in many countries.

Due to the chemical structure and pharmacological properties of the NSAIDs, their application can cause local irritation, burning and itching sensations, and may delay wound healing. In some cases, use of NSAIDs may cause superficial punctate keratitis. [Salva P. et al., 1999; Scuderi B. et al., 2003; Mccarey B. et al., 1995; Stroobants A. et al., 2000; Diestelhorst M. et al., 1996].

New ophthalmic vehicles and delivery systems have been introduced in the last decade which improve the tolerability and increase the efficacy of ocular treatments. Bioadhesive inserts and gels, nanoparticles, nanocapsules, niosomes, liposomes, and microemulsions have been extensively investigated. [U.S. Pat. No. 5,496,811 ("Submicron Emulsions as Ocular Drug Delivery Vehicles") to Aviv H. et al.; U.S. Pat. No. 5,364,632 ("Medicinal Emulsions") to Benita S. and Levy M.; U.S. Pat. No. 5,171,566 ("Flurbiprofen Derivative Ophthalmic Preparation"); and U.S. Pat. No. 4,613,505 ("Ester of Flurbiprofen and Emulsion Containing the Same"), both to Mizushima Y. et al.].

Colloidal ophthalmic compositions show improved tolerance and better transport properties for incorporated drugs [Aggarwal D. et al., 2005; Mainardes R. et al., 2005; De T K et al., 2004; Calvo P. et al., 1996].

Menthol can improve the penetration of indomethacin across the skin in mixtures of indomethacin and menthol by increasing permeability of the skin. Menthol is irritative to the eye, however. Therefore, a mixture of menthol and indomethacin at concentrations high enough to show improved penetration of indomethacin would likely be too painful to the eye to permit a mixture of indomethacin and menthol to feasibly be used in an ophthalmic preparation.

Another disadvantage of indomethacin is that it is unstable at pH greater than 6.0. As such, indomethacin is unstable in the body pH of approximately 7.4.

Due to the limitations of current ophthalmic pharmaceutical compositions which comprise indomethacin or sodium salt of indomethacin, there is a need for an improved ophthalmic pharmaceutical composition of indomethacin that shows both enhanced stability, and lesser negative side effects.

SUMMARY OF THE INVENTION

The inventors have developed ophthalmic pharmaceutical compositions which comprise an ester of indomethacin, such as menthyl ester of indomethacin (MEI). The compositions of the invention show significantly decreased negative side effects and improved stability as compared to other ophthalmic pharmaceutical compositions comprising indomethacin or indomethacin salts. The compositions are more stable at higher pH. These compositions also show enhanced penetration through biological membranes such as through the skin and through the eye.

Accordingly, in one embodiment, the MEI is prepared by esterification of indomethacin with menthol. The resulting compound is then purified by crystallization.

In another embodiment, the purified MEI can be formulated into a colloidal dispersion.

In another embodiment, the purified MEI can be formulated into a suspension.

In another embodiment, MEI can be incorporated into a micellar preparation.

In another embodiment, clear solutions of MEI can be prepared by mixing MEI into a water-based solution.

In yet another embodiment, MEI can be incorporated into an emulsion.

In yet another embodiment, MEI can be incorporated into an emulsion, where the particles of MEI are of submicron size. In one embodiment, the particles could be from 10-1000 nm in diameter. In another embodiment they could be from 15-500 nm in diameter. It will appreciated that other size ranges for the particles of MEI may also work.

In yet another embodiment, MEI can be incorporated into a bioadhesive suspension.

In still yet another embodiment, MEI can be incorporated into a bioadhesive emulsion.

In still yet another embodiment, MEI can be incorporated into a gel.

In still yet another embodiment, the MEI can be incorporated into a gel comprising poloxamer. Poloxamer is a synthetic block copolymer of ethylene oxide and propylene oxide.

In yet another embodiment, a pharmaceutically effective amount of MEI can be applied to an eye to treat inflammation of the eye. Inflammation can be caused by many factors, including, but not limited to, infection, surgery, burn, irritation, injury or other trauma.

Thus the invention provides a method of ophthalmic treatment, including prophylactic treatment, by administering to an eye (wherein the eye is inflamed or may become inflamed) an effective amount of the pharmaceutical composition of the invention comprising a menthyl ester of indomethacin. In one embodiment the effective dose applied is 0.05-5 mg/day/eye.

As such, in one embodiment, the invention provides a pharmaceutical composition comprising a menthyl ester of indomethacin and a pharmaceutically acceptable carrier. In one embodiment, the pharmaceutical composition is an ophthalmic pharmaceutical composition. In one embodiment, the pharmaceutical composition is in the form of a colloidal dispersion. In another embodiment the colloidal dispersion is a suspension, emulsion, or microemulsion. In another embodiment the composition comprises micelles, nanoparticles, nanocapsules, niosomes and/or liposomes comprising menthyl ester of indomethacin. In one embodiment the pharmaceutical composition is a lotion, cream, ointment or solution in non-irritative vehicle. In another embodiment, the amount of menthyl ester of indomethacin in the composition is 0.05-5% (w/w).

In one embodiment, the MEI can be applied topically to the eye.

In one embodiment, the MEI can be applied topically to the eye by way of eye drops.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from reading the detailed description.

DETAILED DESCRIPTION OF A PREFERRED EMBODIMENT

Figure 1:
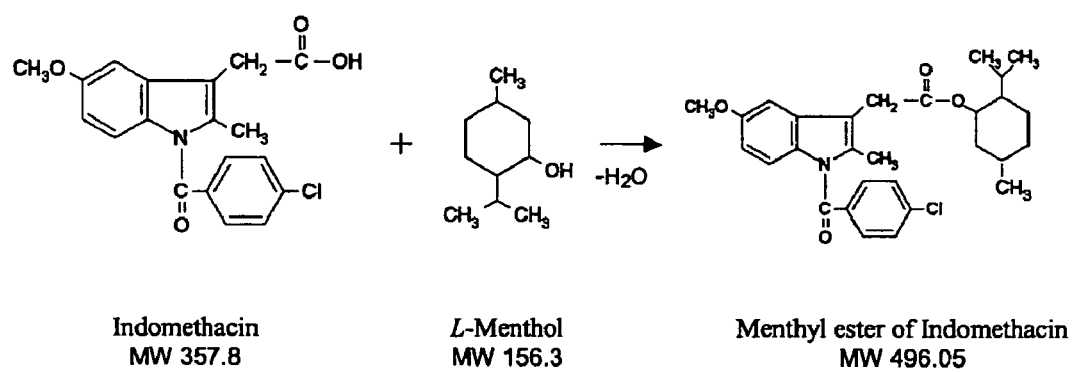
FIG. 1 illustrates the reaction of indomethacin with L-menthol to form the menthyl ester of indomethacin.

Menthyl ester of indomethacin (MEI) was prepared by esterification of indomethacin with menthol. The method of esterification would be apparent to the skilled person working in synthetic chemistry. Suitable methods include condensation in the presence of an acidic catalyst or using a coupling agent, such as carbodiimide, but it will be appreciated that other methods of esterification known to those skilled in the art may be used. The reaction of menthol (2-isopropyl-5-methylcyclohexanol) and indomethacin [1-(4-Chlorobenzoyl)-5-Methoxy-2-methyl-1H-indole-3-acetic acid] yields MEI. The reaction between menthol and indomethacin is depicted in FIG. 1. Any crystalline or amorphous form of indomethacin can be used. Furthermore, any complex, including, but not limited to hydrates, hemihydrates, and alcoholates can be used.

The obtained compound was purified by crystallization from hexane-ethylacetate mixture. Methods of crystallization are known to skilled persons in the art. The chemical structure of the compound was confirmed by elemental analysis, nuclear magnetic resonance (NMR), infrared (IR) analysis, ultraviolet (UV) analysis and mass-spectrometry.

The synthesized prodrug readily hydrolyses in vivo to indomethacin and menthol. The synthesized prodrug also demonstrates low toxicity and irritative properties and pronounced anti-inflammatory properties due to the fast release of indomethacin in the presence of esterases (see FIG. 2 and FIG. 3).

The inventors found that the presence of a menthol moiety in the prodrug molecule increases penetration of the substance through biological membranes, such as human skin, mucosal surfaces and the cornea, and significantly decreases eye irritation.

Several formulations of MEI were prepared, and tested for stability, toxicity, irritative properties and anti-inflammatory activity. Formulations that can be prepared include, but are not limited to, emulsions, microemulsions, liposomes, water based solutions, micellar preparations, suspensions and bioadhesive suspensions. In one embodiment, the end form of the product can include, but is not limited to, lotions, creams, ointments and gels.

In one embodiment, an effective or therapeutically effective amount of the composition is administered. An "effective amount" as used herein means an amount effective, at dosages and for periods of time necessary to achieve the desired results. Administration of a therapeutically effective amount of pharmaceutical compositions of the present invention is defined as an amount effective, at dosages and for periods of time necessary to achieve the desired therapeutic result. For example, an effective or therapeutically effective amount of a substance may vary according to factors such as the disease state, age, sex, and weight of the individual, and the ability of the substance to elicit a desired response in the individual. Dosage regimes may be adjusted to provide the optimum response. For example, several divided doses may be administered daily or the dose may be proportionally reduced as indicated by the exigencies of the therapeutic situation. In addition, an individual skilled in the art will appreciate that various excipients such as those set out in Remington: *The Science and Practice of Pharmacy*, $20^{th}$ edition, [Remington, 2000] may be added to the end topical composition.

Pharmaceutically acceptable carrier as used herein, such as a pharmaceutically acceptable ophthalmic carrier, includes excipients, diluents, adjuvants and vehicles and the like. It generally refers to components of the pharmaceutical composition other than the menthyl ester of indomethacin. In one embodiment, the components can aid in drug delivery, solubility or consistency of the drug for ophthalmic use.

The present invention is described in the following Examples, which are set forth to aid in the understanding of the invention, and should not be construed to limit in any way the scope of the invention.

EXAMPLES

Example 1

Menthyl Ester of Indomethacin (MEI)—Synthesis Description 18 g of indomethacin (50 mmol) and 8 g of natural menthol were dissolved in 200 ml dry toluene. 0.2 g of p-toluenesulfonic acid was added, and the mixture was boiled with a Dean-Stark trap until the required amount of the water was collected. After solvent evaporation, the residue was dissolved in ethylacetate-hexane mixture (1:4) and passed through a 2 cm layer of dry alumina (Beckman II activity level, 40-100 mesh). The solvent was evaporated, and the residue crystallized twice from ethylacetate-hexane 1:10.

MEI is a slightly yellow crystalline substance with a melting point of 86-90° C. It is insoluble in water, but freely soluble in alcohol, methylene chloride and chlorophorm, ethyl acetate, glycerides and other organic solvents. It is poorly soluble in propylene glycol and polyethylene glycol (PEG)-400. The NMR, mass-spectrometry and FT-IR-spectrum results were:

NMR

Found: C, 70.47%; H, 6.98%; N, 2.71%; Cl 7.36%.
Theor. for $C_{29}H_{34}NO_4Cl$: C, 70.22%; H, 6.91%; N, 2.82%; Cl, 7.15%.

Mass-spectra: (MW=496.05)

358 (Indomethacin), 496 ($M^+$), 497 ($MH^+$), 513 ($M^+ + H_2O$), 514($MH^+ + H_2O$)

FT-IR-spectrum (susp. in Nujol), showing the location of each peak: 3582.9 $cm^{-1}$, 2850.8 $cm^{-1}$, 2363.9 $cm^{-1}$, 1732.6 $cm^{-1}$, 1683.9 $cm^{-1}$ 1596.1 $cm^{-1}$, 1525.2 $cm^{-1}$, 1262.0 $cm^{-1}$, 1226.6 $cm^{-1}$, 1171.7 $cm^{-1}$, 1152.2 $cm^{-1}$, 1087.7 $cm^{-1}$, 1075.3 $cm^{-1}$, 1039.5 $cm^{-1}$, 1015.8 $cm^{-1}$, 985.2 $cm^{-1}$, 930.7 $cm^{-1}$, 904.7 $cm^{-1}$.

Example 2

Suspension of MEI (1 mg/ml and 2.5 mg/ml)

Crystallized MEI was dissolved in ethyl alcohol, containing non-ionic surfactant, to form 10% solution by weight (w/w). The prepared solution was diluted with purified water, and then buffer salts. Suspending polymer and preservative were then added and mixed until completely dissolved. The obtained suspensions (see Table 1) showed slow sedimentation and can be easily resuspended.

TABLE 1

| COMPONENTS | Suspension 2-1 | Suspension 2-2 |
|---|---|---|
| MEI | 0.1% | 0.25% |
| Ethyl alcohol USP | 1% | 2.5% |
| TPGS (Tocophersolan USP) | 1.2% | |
| Tween-80 (Polysorbate 80 USP) | | 2.25% |
| Sodium carboxymethylcellulose USP | | 2% |
| Hydroxyethylcellulose USP | 1.5% | |
| Mono and disodium phosphate NF | To pH 6.8 | |

TABLE 1-continued

| COMPONENTS | Suspension 2-1 | Suspension 2-2 |
|---|---|---|
| Chlorobutanol USP | 0.2% | |
| Benzalconium chloride USP | | 0.005% |
| Water purified (USP) | To 100% | |
| Particle size (microscopic estimation) | 2-5 mcm | 1-8 mcm |

Example 3

Micellar Preparation of MEI

Crystallized MEI was dissolved in melted Solutol HS-15 at 65-75° C. After a clear solution was obtained, hot water (75° C.) was added with intensive mixing, and the obtained dispersion was rapidly cooled to room temperature. After cooling, buffer components, glycerin (tonicity agent) and benzalconium chloride (preservative) were added. The prepared micellar formulation was sterilized by filtration through 0.1 mcm membrane filter. The formulation is as shown in Table 2.

TABLE 2

| COMPONENTS | % |
|---|---|
| MEI | 0.1 |
| Solutol ® HS-15 | 5.0 |
| (Polyethoxylated 15-hydroxystearic acid, BASF) | |
| Glycerin USP | 1.1 |
| Monosodium phosphate dihydrate USP/NF | 0.40 |
| Disodium phosphate dihydrate USP/NF | 0.72 |
| Benzalconium chloride USP | 0.01 |
| Water purified (USP) | To 100% |

Example 4

Water Based Solutions of MEI 0.1% clear solutions of MEI can be prepared in 33% w/w water solution of beta-hydroxypropyl-cyclodextrin (beta-HPCD, Encapsin®) or in 16% of 7-sulfobutylester of beta-cyclodextrin (Captisol®) by mixing for 12 hours, followed with 30 minutes sonication and filtration through 0.22 mcm microporous membrane, followed by pH and tonicity adjustment. 0.25% MEI solutions were prepared in 45% Encapsin® and 30% Captisol®, respectively.

Example 5

Emulsions Containing MEI

Crystalline MEI was dissolved in selected oil (containing surfactant) and heated to 45-55° C. The obtained solution was mixed with water phase, heated to 55° C. and the resultant solution, comprised of water, tonicity adjustment agent and preservatives, was emulsified using a high shear mixer of rotor-stator type (for example, the Omni GLH General Laboratory Homogenizer) at 6000-8000 rpm for 5 minutes. The emulsions prepared are shown in Table 3.

TABLE 3

| COMPONENTS | 5-1 | 5-2 | 5-3 | 5-4 | 5-5 % | 5-6 | 5-7 | 5-8 | 5-9 |
|---|---|---|---|---|---|---|---|---|---|
| MEI | 0.1 | 0.25 | 0.25 | 0.25 | 0.25 | 0.25 | 0.1 | 0.25 | 0.25 |
| Medium chain triglycerides USP/NF | 5 | | | | | | | 2 | |
| Tocopherol acetate USP | | | | 2.5 | 2.5 | | 1 | | |
| Acetylated glycerides USP | | | 5 | | | | 2.5 | 3 | 2.5 |
| Tocopherol USP | | 2.5 | | | | | | | |
| Castor oil | | | | | 2.5 | | | | |
| Lecithin USP | | | | | | | 0.5 | | 0.75 |
| Tyloxapol USP | | | | | 1.25 | | | | |
| Cremophor EL USP | 2 | | 2 | | | 2.5 | | | 2.5 |
| Tocophersolan USP | | 1.5 | | 1.25 | | | 1 | | |
| Poloxamer 188 USP | | | | | | | | 2.5 | |
| Polysorbate-80 USP | | | | | | 1 | | | |
| Sodium chloride USP | | | 0.85 | | 0.85 | | | 0.85 | |
| Sodium edetate USP | | | | | | | 0.02 | | 0.01 |
| Methylparaben USP | | | | 0.2 | | | 0.2 | | |
| Benzalconium chloride | 0.005 | 0.01 | | | 0.01 | 0.01 | | 0.01 | 0.005 |
| Alcohol USP | | | | | | | 0.5 | | 0.75 |
| Glycerin USP | 2.2 | 2.2 | 2.2 | | | 2.2 | 1.5 | | 1.0 |
| Water (purified) USP | | | | | To 100% | | | | |

Example 6

Submicron Emulsion of MEI 0.75 g of MEI and 1.0 g of phospholipid (Lecithin USP) were added to 15 g of MCT oil, and the mixture was heated at 50° C.-65° C. to form a clear solution. The solution was mixed with 200 ml of a buffer solution (0.05M phosphate buffer, pH 6.8), and heated to 65° C. Then 4.5 g of glycerol (USP), 0.6 g of methyl paraben and 0.06 g of sodium edetate were added, the volume was adjusted to 300 ml with the said buffer solution, and then the mixture was treated with a rotor-stator type mixer (the Omni GLH) at 6000-8000 rpm for 5 minutes to form a coarse emulsion. This coarse emulsion was further treated using a high pressure homogenizer (Avestin C-5) at 15000-18000 psi (1000-1200 atm) for 5 cycles, and then passed through 0.45 mcm nylon membrane filter. A fine submicron emulsion was obtained.

Example 7

Bioadhesive Suspension of MEI 0.125 g of MEI was dissolved in 2 g of 50% (w/w) alcoholic solution of lecithin USP (Phospholipon S-80), containing 10% of Tocophersolan USP. The prepared mixture was diluted with 42 ml of hot (60° C.) water phase, comprising 1.5% Glycerin USP, 0.01% Sodium Edetate USP and 0.2% of Chlorobutanol USP. The obtained colloidal suspension was immediately mixed with 5 ml of 2% solution of bioadhesive polymer (Hydroxypropyl methylcellulose K4M, Chitosan Lactate or Sodium Hyaluronate) and filtered through 0.45 mcm nylon filter to remove large particles.

Example 8

Bioadhesive Emulsion of MEI

A bioadhesive emulsion of MEI was prepared dissolving sodium hyaluronate (0.4%) in a prepared emulsion (such as the emulsion prepared in Example 5-4). After complete dissolution of the polymer, the bioadhesive emulsion was filtered through 5 mcm nylon membrane filter and autoclaved for 15 minutes at 121° C.

Example 9

Poloxamer Gel of MEI 0.05 g of MEI was dissolved in 5 ml of PEG-400 USP at 60° C. In a separate vessel solution of 7.5 g of Poloxamer 188 USP and 5 g of Poloxamer 407 in 45 ml of cold (5-10° C.) purified water was prepared. Both solutions were combined at room temperature, sonicated for 30 minutes using a sonication bath, cooled and filtrated in cold state (e.g. at 5-10° C.) through 0.45 mcm nylon membrane filter.

Example 10

Comparison of Ocular Irritation Levels

The ocular irritation of MEI in an ophthalmic formulation as compared with an indomethacin-containing ophthalmic preparation has been tested in 3 healthy volunteers. One drop (40-50 mcl) of the tested formulations (0.25% of MEI (as per Example 5-9), 0.1% Indocollyre®, and sterile saline as the control) was placed onto the eye of each volunteer using an appropriate dropper. The interval between sample applications was at least 24 hours The comparative irritation for MEI, indomethacin and other NSAIDs (Indocollyre®) in ophthalmic formulations is set out in Table 4 (volunteers data, n=3):

TABLE 4

|  | Control (Saline) | Indocollyre ® 0.1% | MEI 0.25% (Example 5-9) |
|---|---|---|---|
| Subj. 1 | 1 | 7 | 2 |
| Subj. 2 | 0 | 6 | 1 |
| Subj. 3 | 1 | 7 | 1 |
| Average score | 0.67 | 6.67 | 1.33 |

The irritation scale in the above table ranges from 0-10, with 0 corresponding to no burning or itching, and 10 corresponding to extremely severe burning or itching. Clearly, the ophthalmic formulation comprising MEI showed significantly lower irritation than indomethacin in solution.

Example 11

Pharmacokinetics of MEI in Rats

Figure 2:
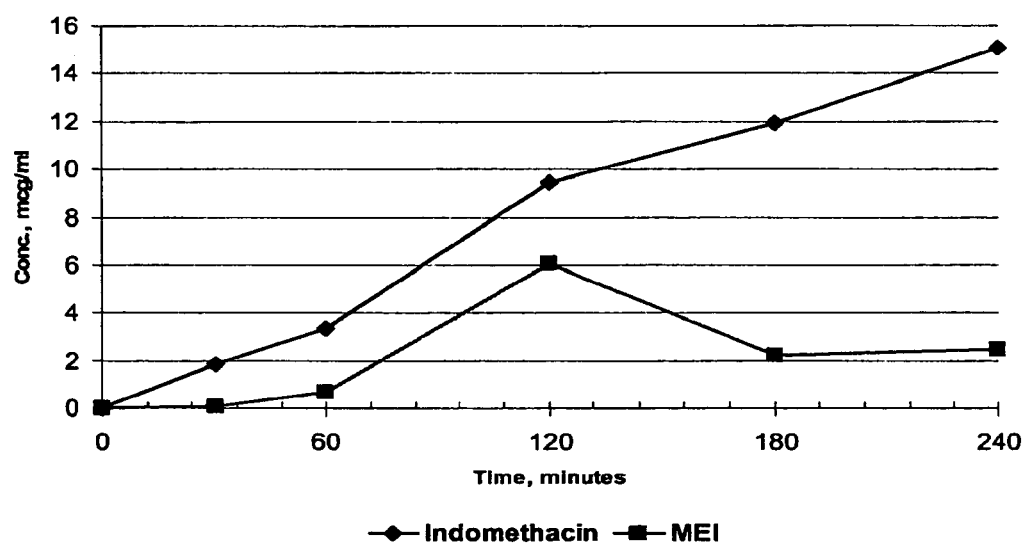
FIG. 2 is a graph illustrating the pharmacokinetics of MEI in Wistar rats after intraperitoneal IP) administration (20 mg/kg, Example 6) as described in Example 11.

As presented in FIG. 2, MEI [20 mg/kg, submicron emulsion and Example 6] injected intraperitoneally into the body of Wistar rats rapidly metabolizes and releases indomethacin for a prolonged period, while the level of the parent substance (i.e. MEI itself), decreases rapidly.

Example 12

Figure 3:
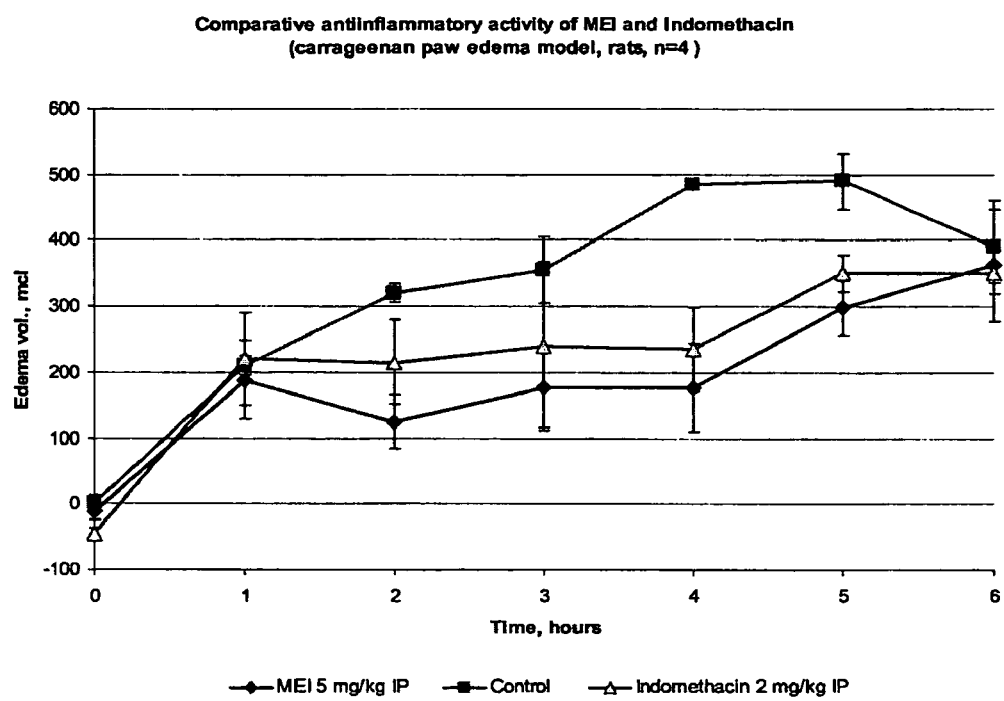
FIG. 3 is a graph illustrating the comparative anti-inflammatory activity of indomethacin and MEI in a carrageenan paw edema model (rats, n=4) as described in Example 12.

Comparative Anti-inflammatory Activity of Indomethacin and MEI in a Carrageenan Model FIG. 3 represents the anti-inflammatory activity of MEI in a carrageenan model. Inflammation in rats (n=4) was caused by injection of 100 microliters of sterile 1% carrageenan solution into a hind paw, originating local edema development with maximum development at 3-4 hours after administration. The contaralateral paw was injected with 100 microliters of saline and used as control. Paw volumes were measured by plethysmometry, (Ugo Basil Plethysmometer, Italy) and the calculated difference in paw volumes indicated the severity of inflammation.

Indomethacin released from intraperitoneally administrated MEI provides a high level of anti-inflammatory activity, and such activity correlates with the dose of administrated substance.

Example 13

Comparative Irritability of Indomethacin and MEI in Eyes

Two healthy volunteers instilled into 30 microliters of 0.1% Indomethacin ophthalmic solution (Indocid® ophthalmic, Merck) into their eye. The next day, 30 microliters of 0.25% MEI in emulsion (Example 5-4) was applied. Sterile saline (30 microliters) was used as a reference before the experiment. The observed results are represented below in arbitrary units.

TABLE 5

|  | Saline | Indomethacin Indocid ® | MEI (Example 5-4) |
|---|---|---|---|
| Mean Irritation Score (0 = no irritation, 4 = severe irritation) | 0.5 | 3.5 | 1.0 |

While the present invention has been described with reference to what is presently considered to be a preferred embodiment, it is to be understood that the invention is not limited to the disclosed embodiment. To the contrary, the invention is intended to cover various modifications and equivalent arrangements included within the spirit and scope of the appended claims.

All publications, patents, and patent applications are herein incorporated by reference in their entireties, to the same extent as if each individual publication, patent, or patent application was specifically and individually indicated to be incorporated by reference in its entirety.

REFERENCES

U.S. Patents
1. U.S. Pat. No. 6,306,890 Kalgutkar, Amit S.; Marnett, Lawrence J. Esters derived from indolealkanols and novel amides derived from indolealkylamides that are selective COX-2 inhibitors
2. U.S. Pat. No. 6,762,182 Kalgutkar, Amit S.; Marnett, Lawrence J. Converting COX inhibition compounds that are not COX-2 selective inhibitors to derivatives that are COX-2 selective inhibitors
3. U.S. Pat. No. 5,496,811 Aviv, H.; Friedman, D.; Bar-Ilan, A.; Vered, M. Submicron emulsions as ocular drug delivery vehicles
4. U.S. Pat. No. 5,364,632 Benita, S.; Levy, M. Medicinal emulsions
5. U.S. Pat. No. 5,171,566 Mizushima, Y., et al. Flurbiprofen derivative ophthalmic preparation
6. U.S. Pat. No. 4,613,505 Mizushima, Y., et al. Ester of flurbiprofen and emulsion containing the same
7. U.S. Pat. No. 5,998,465 Hellberg, M., et al. Esters of non-steroidal anti-flammatory carboxylic acids Articles
1. Salva P, Costa J, Andreu D, Notivol R, Martinez M. TOLERABILITY AND SAFETY OF 0.1% DICLOFENAC PLUS 0.3% TOBRAMYCIN FIXED-DOSE OPHTHALMIC SOLUTION: A RANDOMIZED, COMPARATIVE, CONTROLLED STUDY IN HEALTHY VOLUNTEERS. Methods Find Exp Clin Pharmacol. April 1999; 21(3):203-8.
2. Scuderi B, Driussi G B, Chizzolini M, Salvetat M L, Beltrame G. EFFECTIVENESS AND TOLERANCE OF PIROXICAM 0.5% AND DICLOFENAC SODIUM 0.1% IN CONTROLLING INFLAMMATION AFTER CATARACT SURGERY. Eur J Ophthalmol. July 2003; 13(6):536-40.
3. Mccarey B., Napalkov J., Pippen P., Koester J. and Al Reavers T. CORNEAL WOUND HEALING STRENGTH WITH TOPICAL ANTIINFLAMMATORY DRUGS. Cornea, 1995, 14: 290-294.
4. Stroobants A., Fabre K. Maudgal P. EFFECT OF NON-STEROIDAL ANTI-INFLAMMATORY DRUGS (NSAID) ON THE RABBIT CORNEAL EPITHELIUM STUDIED BY SCANNING ELECTRON MICROSCOPY Bull. Soc. Belge Ophtalmol., 276, 73-81, 2000.
5. Diestelhorst M, Schmidl B, Konen W, Mester U, Raj P S. EFFICACY AND TOLERANCE OF DICLOFENAC SODIUM 0.1%, FLURBIPROFEN 0.03%, AND INDOMETHACIN 1.0% IN CONTROLLING POST-OPERATIVE INFLAMMATION. J Cataract Refract Surg. 1996;22 Suppl 1:788-93.
6. Aggarwal D, Kaur I P. IMPROVED PHARMACODYNAMICS OF TIMOLOL MALEATE FROM A MUCOADHESIVE NIOSOMAL OPHTHALMIC DRUG DELIVERY SYSTEM. Int J Pharm. Feb. 16, 2005; 290(1-2):155-9.
7. Mainardes R M, Urban M C, Cinto P O, Khalil N M, Chaud M V, Evangelista R C, Gremiao M P. COLLOIDAL CARRIERS FOR OPHTHALMIC DRUG DELIVERY. Curr Drug Targets. May 2005; 6(3):363-71.
8. De T K, Bergey E J, Chung S J, Rodman D J, Bharali D J, Prasad P N. POLYCARBOXYLIC ACID NANOPARTICLES FOR OPHTHALMIC DRUG DELIVERY: AN EX VIVO EVALUATION WITH HUMAN CORNEA. J Microencapsul. December 2004; 21(8): 841-55.
9. Calvo P, Alonso M J, Vila-Jato J L, Robinson J R. IMPROVED OCULAR BIOAVAILABILITY OF INDOMETHACIN BY NOVEL OCULAR DRUG CARRIERS. J Pharm Pharmacol. November 1996; 48(11):1147-52.
10. Remington: THE SCIENCE AND PRACTICE OF PHARMACY, 20$^{th}$ edition, Lippincott, Williams and Wilkins, Philadelphia, 2000.

What is claimed is:

1. A pharmaceutical ophthalmic composition comprising a menthyl ester of indomethacin and a pharmaceutically acceptable carrier.

2. The pharmaceutical composition of claim 1, wherein the concentration of the menthyl ester of indomethacin is 0.05-5.0% w/w.

3. A method for the treatment of ophthalmic inflammation in a subject in need thereof comprising the step of: applying to the eye a pharmaceutically effective amount of a pharmaceutcal ophthalmic composition comprising a menthyl ester of indomethacin and a pharmaceutically acceptable carrier.

4. The method of claim 3, wherein the concentration of menthyl ester of indomethacin in the pharmaceutical ophthalmic composition is in the range of 0.05-5.0% w/w.

5. The method of claim 3, wherein the dose of the menthyl ester of indomethacin administered in pharmaceutical ophthalmic composition is in the range of 0.05-5 mg of indomethacin per eye per day.

6. The method of claim 3, wherein the composition is administered topically to the eye.

* * * * *